(12) United States Patent
Itoh et al.

(10) Patent No.: US 8,440,109 B2
(45) Date of Patent: May 14, 2013

(54) FULLERENE DERIVATIVE

(75) Inventors: Toshiyuki Itoh, Tottori (JP); Yasunori Uetani, Tsukuba (JP)

(73) Assignees: Sumitomo Chemical Company, Limited, Tokyo (JP); National University Corporation Tottori University, Tottori (JP)

( * ) Notice: Subject to any disclaimer, the term of this patent is extended or adjusted under 35 U.S.C. 154(b) by 374 days.

(21) Appl. No.: 12/677,445

(22) PCT Filed: Sep. 11, 2008

(86) PCT No.: PCT/JP2008/066395
§ 371 (c)(1),
(2), (4) Date: Mar. 10, 2010

(87) PCT Pub. No.: WO2009/035024
PCT Pub. Date: Mar. 19, 2009

(65) Prior Publication Data
US 2011/0001093 A1    Jan. 6, 2011

(30) Foreign Application Priority Data

Sep. 12, 2007  (JP) ................................. 2007-236372
May 15, 2008  (JP) ................................. 2008-128098

(51) Int. Cl.
*H01B 1/12* (2006.01)

(52) U.S. Cl.
USPC ........... 252/511; 252/500; 252/510; 548/417; 977/738; 977/948

(58) Field of Classification Search ............ 252/500, 252/510, 511; 548/417; 977/738, 948
See application file for complete search history.

(56) References Cited

U.S. PATENT DOCUMENTS 6,162,926 A * 12/2000 Murphy et al. ............... 548/417
6,399,785 B1 * 6/2002 Murphy et al. ............... 506/15
6,448,412 B1 * 9/2002 Murphy et al. ............... 506/15
6,949,660 B2 * 9/2005 Chiang et al. ................. 548/517
8,092,773 B2 * 1/2012 Nakanishi et al. ......... 423/445 B
2006/0289058 A1 * 12/2006 Skabara et al. ............... 136/263
2011/0193072 A1 * 8/2011 Itoh et al. ...................... 257/40
2011/0193073 A1 * 8/2011 Itoh et al. ...................... 257/40
2012/0216867 A1 * 8/2012 Ito et al. ........................ 136/263

FOREIGN PATENT DOCUMENTS

| JP | 2000290278 A | * 10/2000 |
| JP | 2005-116617 A | 4/2005 |
| JP | 2006-290788 A | 10/2006 |

OTHER PUBLICATIONS

Kordatos et al., "Novel Functional Fullerene Materials: Fullerenes as Energy Acceptors", Chemical Monthly, 132, 63-69 (2001).*
Office Action issued Nov. 9, 2011, in Chinese Patent Application No. 200880106540 with English translation.
Susanna Bosi et al., "Synthesis of Novel Fullerene Derivatives for Potential Use in Optical Limiting", Nonlinear Optics, 2001, pp. 367-376, vol. 27, No. 1-4.
Pei Wang et al., "Substituents effect on the nonlinear optical properties of $C_{60}$ derivatives", Optics Communications, Jun. 1, 2001, pp. 387-391, vol. 192, No. 3-6.
Peter Brough et al.,"[60] Fullerene-Pyrrolidine-N-oxides", Journal of Organic Chemistry, 2006, pp. 2014-2020, vol. 71, No. 5.
Franz Padinger et al., "Effects of Postproduction Treatment on Plastic Solar Cells", Advanced Function Materials, Jan. 2003, pp. 85-88, vol. 13, No. 1.
Maurizio Prato et al., "Fulleropyrrolidines: A Family of Full-Fledged Fullerene Derivatives", Accounts of Chemical Research, Sep. 1998, pp. 519-526, vol. 31, No. 9.
Chinese Office Action issued on Jul. 11, 2012 by the Chinese Patent Office in Chinese Patent Application No. 200880106540.0.

* cited by examiner

*Primary Examiner* — Douglas McGinty
(74) *Attorney, Agent, or Firm* — Sughrue Mion, PLLC

(57) ABSTRACT

The present invention relates to an organic photoelectric conversion device comprising a layer comprising a fullerene derivative represented by formula (1).

5 Claims, No Drawings

FULLERENE DERIVATIVE

TECHNICAL FIELD

The present invention relates to a fullerene derivative and an organic photoelectric conversion device using the same.

BACKGROUND ART

Organic semiconductor materials having charge (electron and hole) transport properties have been studied for application to organic photoelectric conversion devices (organic solar cells, optical sensors, and the like) and the like. For example, organic solar cells using fullerene derivatives have been investigated. For example, [6,6]-phenyl C61-butyric acid methyl ester (hereinafter sometimes referred to as [60]-PCBM) has been known as a fullerene derivative (see NON-PATENT DOCUMENT 1).
NON-PATENT DOCUMENT 1: Advanced Functional Materials, Vol. 13, p. 85 (2003)

DISCLOSURE OF THE INVENTION

Problems to be Solved by the Invention

However, a problem of an organic photoelectric conversion device comprising [60]-PCBM is that the conversion efficiency is not always sufficient.
Accordingly, it is an object of the present invention to provide an organic photoelectric conversion device having high conversion efficiency. It is another object of the present invention to provide a fullerene derivative having excellent solubility in organic solvents.

Means for Solving the Problems

First, the present invention provides an organic photoelectric conversion device comprising a layer comprising a fullerene derivative represented by the following formula (1):

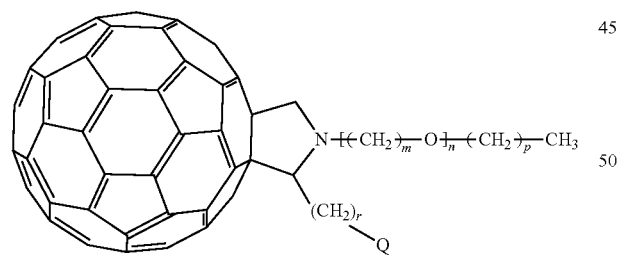

(1)

wherein m represents an integer of 1 to 6, n represents an integer of 1 to 4, p represents an integer of 0 to 5, and r represents an integer of 0 to 4; Q represents a group represented by the following formula (2) or (3); and when there is a plurality of m, the m may be the same or different,

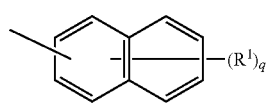

(2)

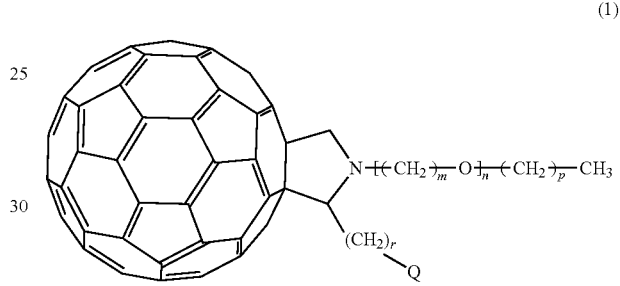

(3)

wherein $R^1$ and $R^2$ each independently represent a halogen atom, an alkyl group, an alkoxy group, or an aryl group; a hydrogen atom included in these groups may be replaced by a halogen atom; q represents an integer of 0 to 7, and v represents an integer of 0 to 5; when there is a plurality of $R^1$, the $R^1$ may be the same or different; and when there is a plurality of $R^2$, the $R^2$ may be the same or different.

Secondly, the present invention provides a composition comprising a fullerene derivative represented by the following formula (1) and an electron-donating compound,

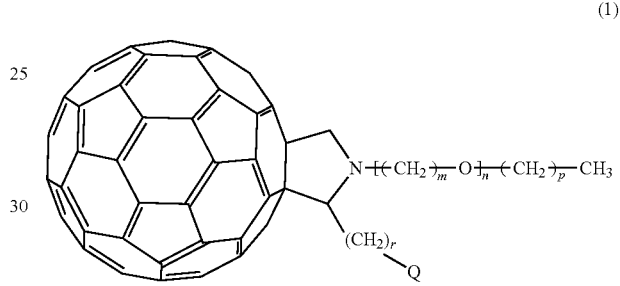

(1)

wherein m represents an integer of 1 to 6, n represents an integer of 1 to 4, p represents an integer of 0 to 5, and r represents an integer of 0 to 4; Q represents a group represented by the following formula (2) or (3); and when there is a plurality of m, the m may be the same or different,

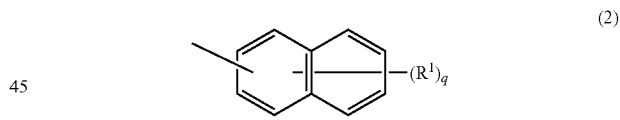

(2)

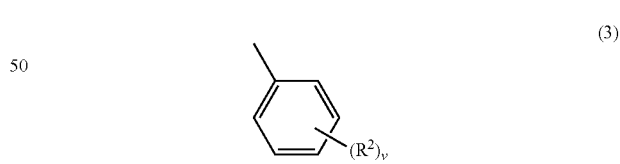

(3)

wherein $R^1$ and $R^2$ each independently represent a halogen atom, an alkyl group, an alkoxy group, or an aryl group; a hydrogen atom included in these groups may be replaced by a halogen atom; q represents an integer of 0 to 7, and v represents an integer of 0 to 5; when there is a plurality of $R^1$, the $R^1$ may be the same or different; and when there is a plurality of $R^2$, the $R^2$ may be the same or different.

Thirdly, the present invention provides an organic photoelectric conversion device comprising a layer comprising the composition.

Fourthly, the present invention provides a fullerene derivative represented by the following formula (4):

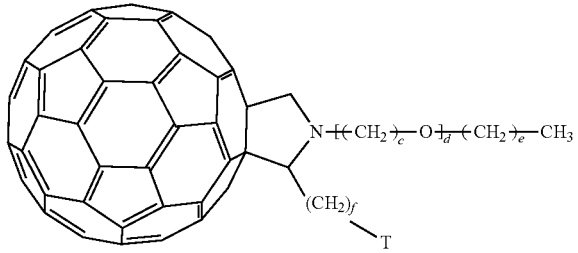
(4)

wherein c represents an integer of 1 to 6, d represents an integer of 1 to 4, e represents an integer of 0 to 5, and f represents an integer of 0 to 4; T represents a group represented by the following formula (5) or (6); and when there is a plurality of c, the c may be the same or different,

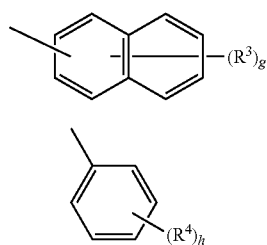
(5)

(6)

wherein $R^3$ and $R^4$ each independently represent a halogen atom, an alkyl group, an alkoxy group, or an aryl group; a hydrogen atom included in these groups may be replaced by a halogen atom; g represents an integer of 0 to 7, and h represents an integer of 0 to 5, provided that when h is 0, f is an integer of 1 to 4; when there is a plurality of $R^3$, the $R^3$ may be the same or different; and when there is a plurality of $R^4$, the $R^4$ may be the same or different.

Advantage of the Invention

The organic photoelectric conversion device of the present invention has high conversion efficiency.

BEST MODE FOR CARRYING OUT THE INVENTION

The present invention will be described below in detail.
<Fullerene Derivative Used in Organic Photoelectric Conversion Device>

The organic photoelectric conversion device of the present invention comprises a layer comprising a fullerene derivative represented by the above formula (1). The fullerene derivative is a $C_{60}$ fullerene derivative. In the above formula (1), Q represents a group represented by the above formula (2) or (3).

When the fullerene derivative used in the organic photoelectric conversion device of the present invention has a group represented by the above formula (2), $R^1$ in the above formula (2) represents a halogen atom, an alkyl group, an alkoxy group, or an aryl group. A hydrogen atom included in these groups may be replaced by a halogen atom. When there is a plurality of $R^1$, the $R^1$ may be the same or different.

The alkyl group represented by $R^1$ in the above formula (2) generally has 1 to 20 carbon atoms, may be linear or branched, and may be a cycloalkyl group. Specific examples of the alkyl group include a methyl group, an ethyl group, an n-propyl group, an isopropyl group, an n-butyl group, an isobutyl group, a t-butyl group, an s-butyl group, a 3-methylbutyl group, an n-pentyl group, an n-hexyl group, a 2-ethylhexyl group, an n-heptyl group, an n-octyl group, an n-nonyl group, an n-decyl group, and an n-lauryl group. A hydrogen atom in the above alkyl group may be replaced by a halogen atom, examples of which include a monohalomethyl group, a dihalomethyl group, a trihalomethyl group, and a pentahaloethyl group. Preferably, a hydrogen atom is replaced by a fluorine atom among halogen atoms. Examples of the alkyl group in which a hydrogen atom is replaced by a fluorine atom include a trifluoromethyl group, a pentafluoroethyl group, a perfluorobutyl group, a perfluorohexyl group, and a perfluorooctyl group.

The alkoxy group represented by $R^1$ in the above formula (2) generally has 1 to 20 carbon atoms, may be linear or branched, and may be a cycloalkyloxy group. Specific examples of the alkoxy group include a methoxy group, an ethoxy group, an n-propyloxy group, an isopropyloxy group, an n-butoxy group, an isobutoxy group, an s-butoxy group, a t-butoxy group, an n-pentyloxy group, an n-hexyloxy group, a cyclohexyloxy group, an n-heptyloxy group, an n-octyloxy group, a 2-ethylhexyloxy group, an n-nonyloxy group, an n-decyloxy group, a 3,7-dimethyloctyloxy group, and an n-lauryloxy group. A hydrogen atom in the above alkoxy group may be replaced by a halogen atom. Preferably, a hydrogen atom is replaced by a fluorine atom among halogen atoms. Examples of the alkoxy group in which a hydrogen atom is replaced by a fluorine atom include a trifluoromethoxy group, a pentafluoroethoxy group, a perfluorobutoxy group, a perfluorohexyl group, and a perfluorooctyl group.

The aryl group represented by $R^1$ in the above formula (2) generally has 6 to 60 carbon atoms and may have a substituent. Examples of the substituent of the aryl group include a linear or branched alkyl group having 1 to 20 carbon atoms, or a cycloalkyl group having 1 to 20 carbon atoms, and an alkoxy group comprising in its structure a linear or branched alkyl group having 1 to 20 carbon atoms, or a cycloalkyl group having 1 to 20 carbon atoms. Specific examples of the aryl group include a phenyl group, a $C_1$ to $C_{12}$ alkoxyphenyl group ($C_1$ to $C_{12}$ indicates having 1 to 12 carbon atoms. The same applies hereinafter.), a $C_1$ to $C_{12}$ alkylphenyl group, a 1-naphthyl group, and a 2-naphthyl group. An aryl group having 6 to 20 carbon atoms is preferred, and a $C_1$ to $C_{12}$ alkoxyphenyl group, and a $C_1$ to $C_{12}$ alkylphenyl group are more preferred. A hydrogen atom in the above aryl group may be replaced by a halogen atom. Preferably, a hydrogen atom is replaced by a fluorine atom among halogen atoms.

Examples of the halogen atom represented by $R^1$ in the above formula (2) include a fluorine atom, a chlorine atom, a bromine atom, and an iodine atom. In terms of conversion efficiency, a fluorine atom is preferred.

In the above formula (1), m represents an integer of 1 to 6. When there is a plurality of m, the m may be the same or different. In terms of the ease of availability of the raw materials, m is preferably 2. p represents an integer of 0 to 5. In terms of charge transport properties, p is preferably an integer of 0 to 3. n represents an integer of 1 to 4, and r represents an integer of 0 to 4.

In the above formula (2), q represents an integer of 0 to 7.

Specific examples of the fullerene derivative having a group represented by the above formula (2) include the following compounds.
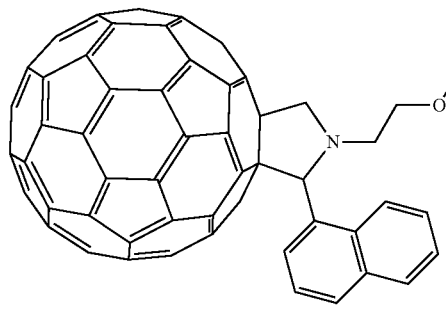
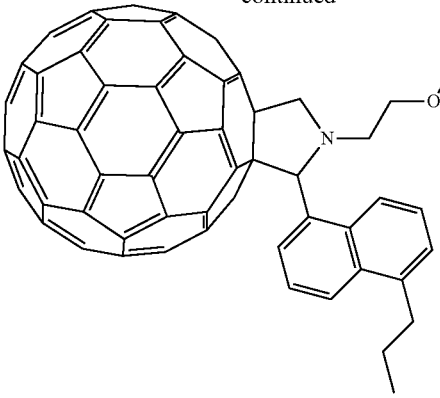
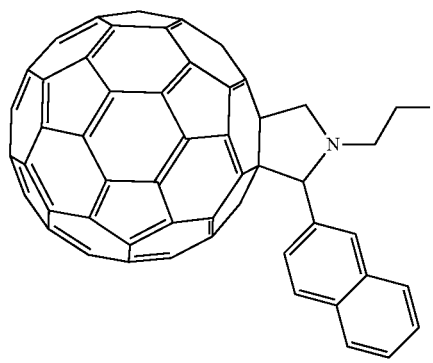
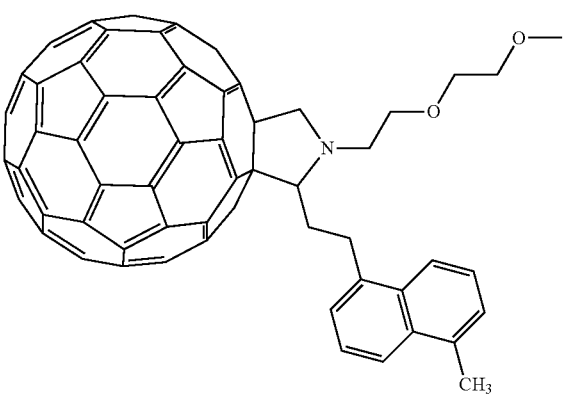
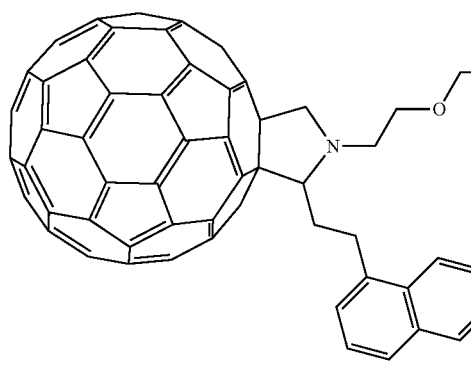
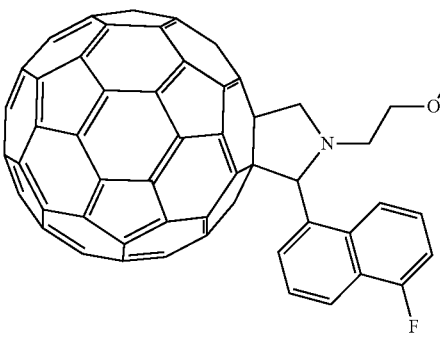
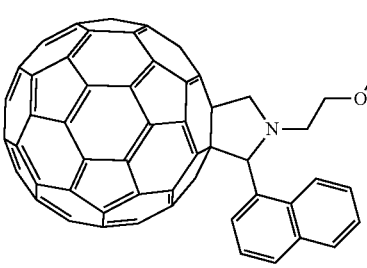
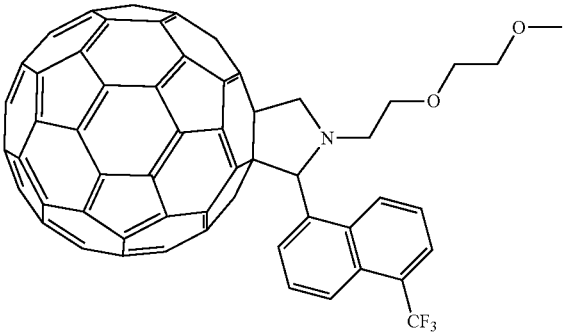

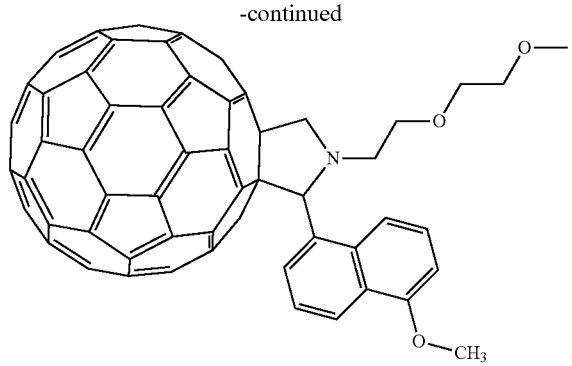

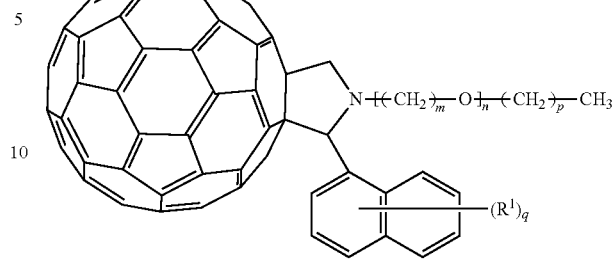

(7)

wHerein $R^1$, m, n, p, and q represent the same meanings as described above.

In the above formula (7), m is preferably 2, n is preferably 2, p is preferably 0, and q is preferably 0 or 1, in terms of conversion efficiency. $R^1$ is preferably a fluorine atom or an alkyl group having 1 to 4 carbon atoms. The alkyl group may be substituted with a fluorine atom.

When the fullerene derivative used in the organic photoelectric conversion device of the present invention has a group represented by the above formula (3), $R^2$ in the above formula (3) represents a halogen atom, an alkyl group, an alkoxy group, or an aryl group. A hydrogen atom included in these groups may be replaced by a fluorine atom. When there is a plurality of $R^2$, the $R^2$ may be the same or different.

The alkyl group represented by $R^2$ in the above formula (3) generally has 1 to 20 carbon atoms and includes the same groups as the alkyl groups described for the above-described $R^1$.

The alkoxy group represented by $R^2$ in the above formula (3) generally has 1 to 20 carbon atoms and includes the same groups as the alkoxy groups described for the above-described $R^1$.

The aryl group represented by $R^2$ in the above formula (3) generally has 6 to 60 carbon atoms and may have a substituent. Examples of the aryl group include the same groups as the aryl groups described for the above-described $R^1$.

Examples of the halogen atom represented by $R^2$ in the above formula (3) include a fluorine atom, a chlorine atom, a bromine atom, and an iodine atom. In terms of conversion efficiency, a fluorine atom is preferred.

In the above formula (3), v represents an integer of 0 to 5. In terms of conversion efficiency, v is preferably 0 or 1.

In terms of conversion efficiency, $R^2$ is preferably an alkyl group or a halogen atom, and more preferably a methyl group or a fluorine atom.

Specific examples of the fullerene derivative having a group represented by the above formula (3) include the following compounds.

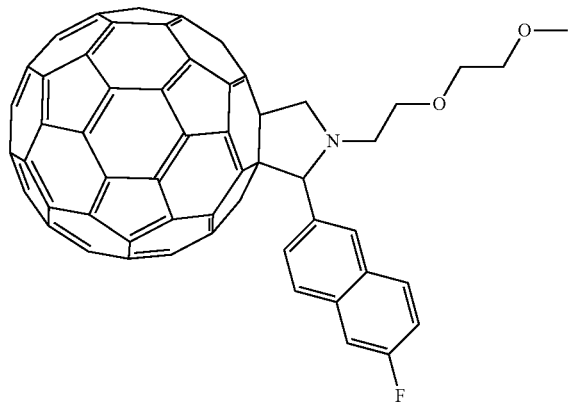

Among the fullerene derivatives having a group represented by the above formula (2), fullerene derivatives represented by the following formula (7) are preferred in terms of conversion efficiency.

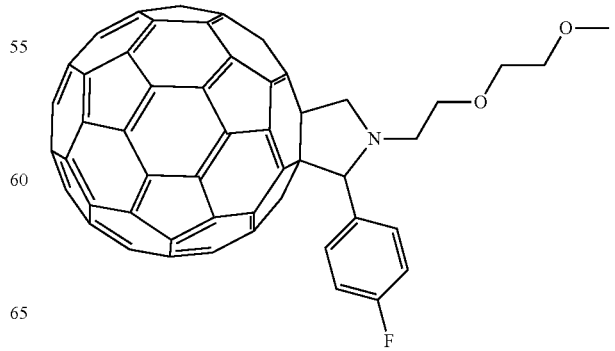

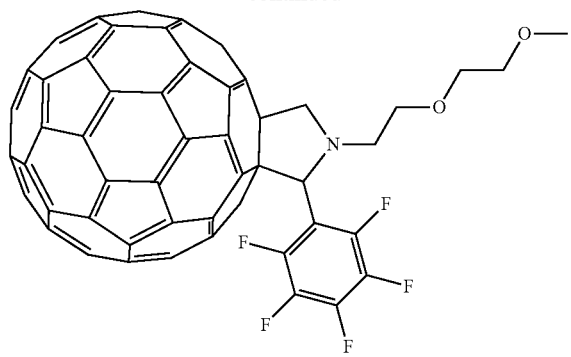
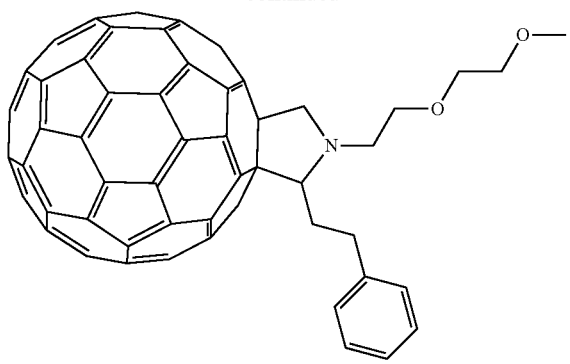
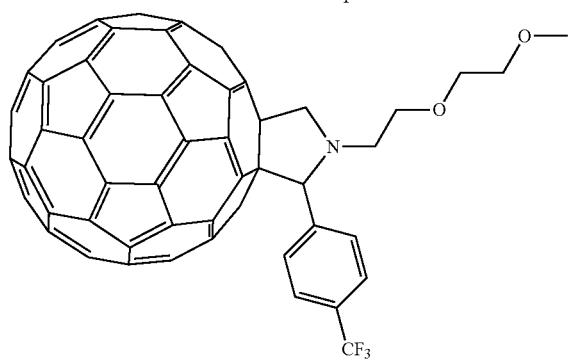
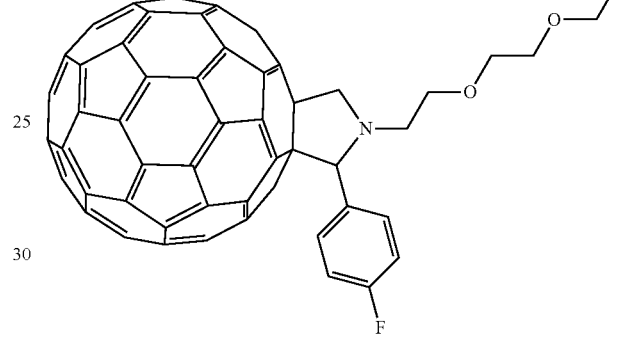
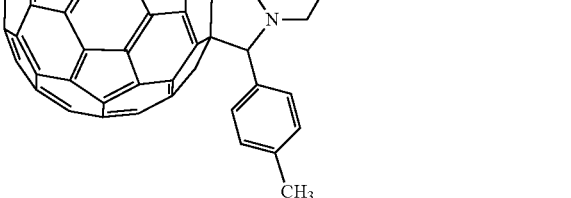
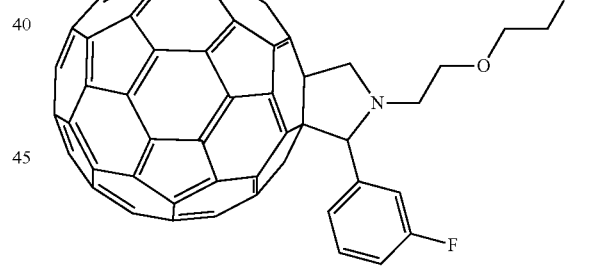
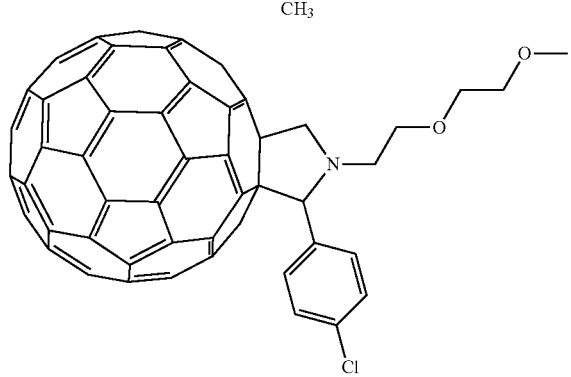
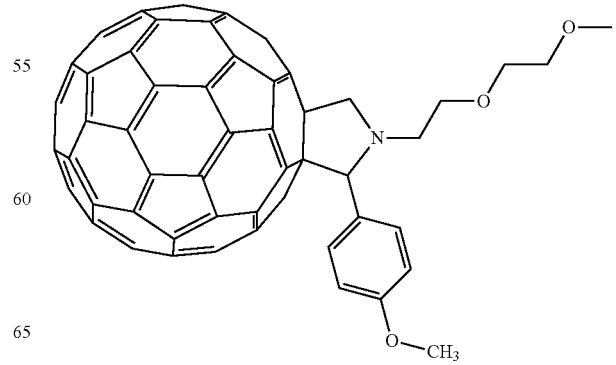

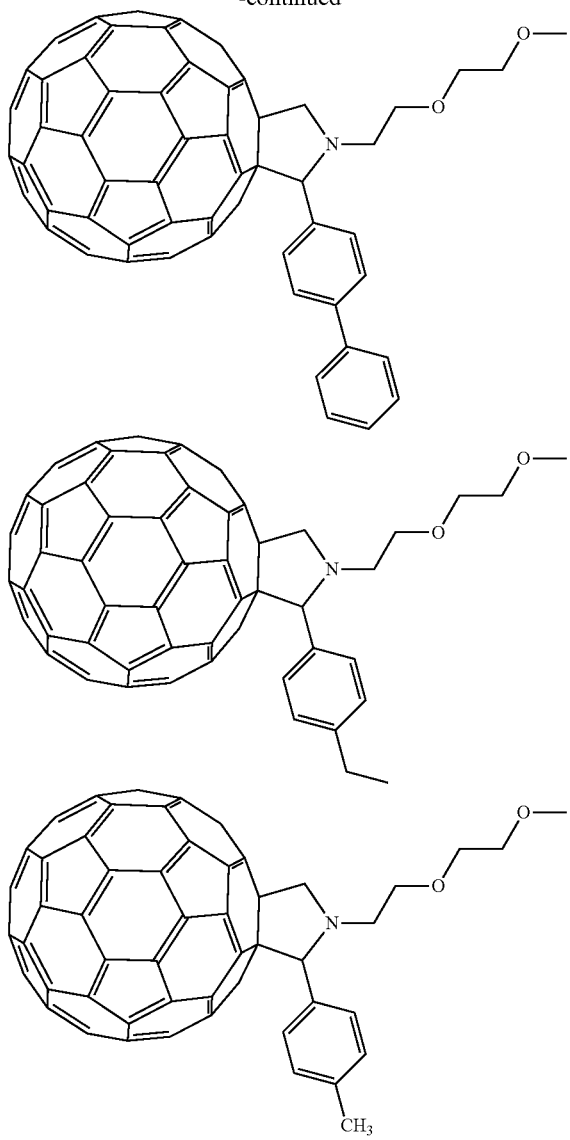

Among the fullerene derivatives having a group represented by the above formula (3), fullerene derivatives represented by the following formula (8) are preferred in terms of conversion efficiency.

(8)

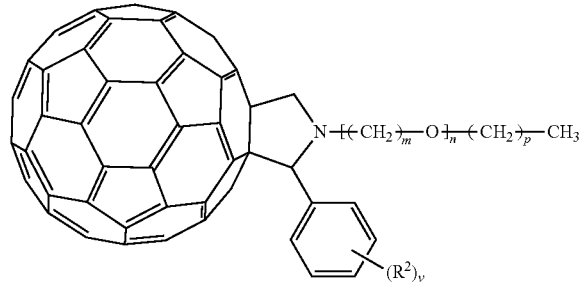

wherein $R^2$, m, n, p, and v represent the same meanings as described above.

In the above formula (8), m is preferably 2, n is preferably 2, p is preferably 0, and v is preferably 0 or 1, in terms of conversion efficiency. $R^2$ is preferably a halogen atom or an alkyl group.

Among the fullerene derivatives represented by the above formula (8), fullerene derivatives represented by the following formula (9) are preferred in terms of conversion efficiency.

(9)

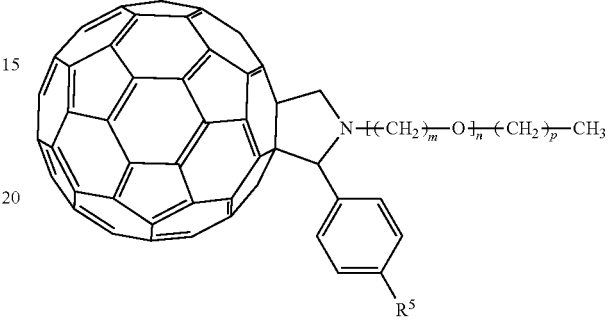

wherein m, n, and p represent the same meanings as described above; and $R^5$ represents a fluorine atom or an alkyl group having 1 to 4 carbon atoms.

In the above formula (9), m is preferably 2, n is preferably 2, and p is preferably 0, in terms of conversion efficiency. $R^5$ is preferably a fluorine atom or a methyl group.

For a method for synthesizing the fullerene derivative represented by the above formula (1), for example, the fullerene derivative can be synthesized by the 1,3-dipolar cycloaddition reaction of $C_{60}$ fullerene and iminium cations produced by the decarboxylation of imine produced from a glycine derivative and aldehyde (Prato reaction, Accounts of Chemical Research, Vol. 31, 519-526 (1998)).

Examples of the glycine derivative used here include N-methoxymethylglycine and N-(2-(2-methoxyethoxy)ethyl)glycine. The amount of these glycine derivatives used is generally in the range of 0.1 to 10 moles, preferably 0.5 to 3 moles, with respect to 1 mole of fullerene.

Examples of aldehyde, the other raw material of the substituent, include benzaldehyde and naphthoaldehyde. The amount of these aldehydes used is generally in the range of 0.1 to 10 moles, preferably 0.5 to 4 moles, with respect to 1 mole of fullerene.

Generally, this reaction is performed in a solvent. In this case, as the solvent, a solvent inert to this reaction, for example, toluene, xylene, hexane, octane, or chlorobenzene, is used. The amount of the solvent used is generally in the range of 1 to 100000 times by weight the amount of fullerene.

In reaction, for example, a glycine derivative, aldehyde, and fullerene should be mixed in a solvent and reacted by heating. The reaction temperature is generally in the range of 50 to 350° C. The reaction time is generally 30 minutes to 50 hours.

After the heating reaction, the reaction mixture is allowed to cool to room temperature, and the solvent is evaporated under reduced pressure by a rotary evaporator. The obtained solids are separated and purified by silica gel flash column chromatography, thereby, the target fullerene derivative can be obtained.

<Organic Photoelectric Conversion Device>

The organic photoelectric conversion device of the present invention comprises a pair of electrodes, at least one of which is transparent or semitransparent, and a layer comprising the fullerene derivative used in the present invention, between the electrodes. The fullerene derivative used in the present invention can be used as an electron-accepting compound and as an electron-donating compound, but is preferably used as an electron-accepting compound.

Next, the operation mechanism of the organic photoelectric conversion device will be described. Light energy entering from the transparent or semitransparent electrode is absorbed by the electron-accepting compound and/or the electron-donating compound to produce excitons in which an electron and a hole are bound. When the produced excitons move and reach the heterojunction interface where the electron-accepting compound and the electron-donating compound are adjacent to each other, electrons and holes separate, due to their difference in HOMO energy and LUMO energy at the interface, to generate charges (electrons and holes) that can move independently. The generated charges move to the electrodes respectively, thereby, the charges can be extracted as electric energy (current) to the outside.

As specific examples of the organic photoelectric conversion device of the present invention, either of the following is preferred:

1. an organic photoelectric conversion device comprising a pair of electrodes, at least one of which is transparent or semitransparent, a first layer provided between the electrodes and containing the fullerene derivative used in the present invention, as an electron-accepting compound, and a second layer containing an electron-donating compound, provided adjacent to the first layer; and
2. an organic photoelectric conversion device comprising a pair of electrodes, at least one of which is transparent or semitransparent, and at least one layer provided between the electrodes and containing the fullerene derivative used in the present invention, as an electron-accepting compound, and an electron-donating compound.

In terms of comprising many heterojunction interfaces, the organic photoelectric conversion device of the above 2. is preferred. Also, in the organic photoelectric conversion device of the present invention, an additional layer may be provided between at least one electrode and the layer comprising the fullerene derivative used in the present invention. Examples of the additional layer include a charge transport layer for transporting holes or electrons.

In the organic photoelectric conversion device of the above 2, the proportion of the fullerene derivative in the organic layer containing the fullerene derivative and the electron-donating compound is preferably 10 to 1000 parts by weight, more preferably 50 to 500 parts by weight, based on 100 parts by weight of the electron-donating compound.

The layer comprising the fullerene derivative used in the organic photoelectric conversion device of the present invention is preferably formed of an organic thin film comprising the fullerene derivative. The thickness of the organic thin film is generally 1 nm to 100 μm, preferably 2 nm to 1000 nm, more preferably 5 nm to 500 nm, and further preferably 20 nm to 200 nm.

The above electron-donating compound is preferably a polymer compound, in terms of coating properties. Examples thereof include polyvinylcarbazole and its derivatives, polysilane and its derivatives, polysiloxane derivatives having aromatic amine in the side chain or the main chain, polyaniline and its derivatives, polythiophene and its derivatives, polypyrrole and its derivatives, polyphenylenevinylene and its derivatives, polythienylenevinylene and its derivatives, and polyfluorene and its derivatives.

The present invention also relates to a composition comprising the above fullerene derivative and the above electron-donating compound, which is used for forming the organic photoelectric conversion device of the present invention.

In terms of conversion efficiency, the electron-donating compound used in the organic photoelectric conversion device is preferably a polymer compound having a repeating unit selected from the group consisting of the following formula (10) and the following formula (11), more preferably a polymer compound having a repeating unit represented by the following formula (10):

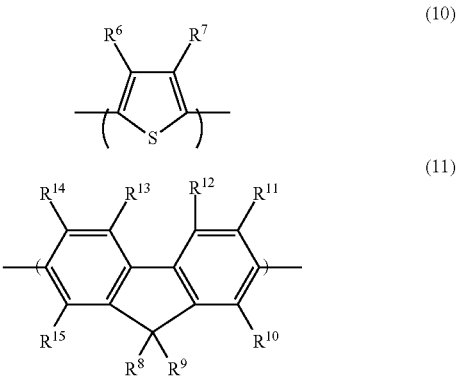

wherein $R^6$, $R^7$, $R^8$, $R^9$, $R^{10}$, $R^{11}$, $R^{12}$, $R^{13}$, $R^{14}$, and $R^{15}$ each independently represent a hydrogen atom, an alkyl group, an alkoxy group, or an aryl group.

When $R^6$ and $R^7$ in the above formula (10) are alkyl groups, specific examples of the alkyl groups include the same alkyl groups as illustrated for the above-described $R^1$. When $R^6$ and $R^7$ are alkoxy groups, specific examples of the alkoxy groups include the same alkoxy groups as illustrated for the above-described $R^1$. When $R^6$ and $R^7$ are aryl groups, specific examples of the aryl groups include the same aryl groups as illustrated for the above-described $R^1$.

In the above formula (10), at least one of $R^6$ and $R^7$ is preferably an alkyl group having 1 to 20 carbon atoms, more preferably an alkyl group having 4 to 8 carbon atoms, in terms of conversion efficiency.

When $R^8$ to $R^{15}$ in the above formula (11) are alkyl groups, specific examples of the alkyl groups include the same alkyl groups as illustrated for the above-described $R^1$. When $R^8$ to $R^{15}$ are alkoxy groups, specific examples of the alkoxy groups include the same alkoxy groups as illustrated for the above-described $R^1$. When $R^8$ to $R^{15}$ are aryl groups, specific examples of the aryl groups include the same aryl groups as illustrated for the above-described $R^1$.

In the above formula (11), $R^{10}$ to $R^{15}$ are preferably hydrogen atoms, in terms of the ease of synthesis of the monomer. Also, in terms of conversion efficiency, $R^8$ and $R^9$ are preferably an alkyl group having 1 to 20 carbon atoms, or an aryl group having 6 to 20 carbon atoms, more preferably an alkyl group having 5 to 8 carbon atoms, or an aryl group having 6 to 15 carbon atoms.

The organic photoelectric conversion device of the present invention is generally formed on a substrate. This substrate should be one that does not change when electrodes are formed, and a layer of an organic substance is formed. Examples of the material of the substrate include glass, plastic, a polymer film, and silicon. In the case of an opaque substrate, the opposite electrode (that is, the electrode far from the substrate) is preferably transparent or semitransparent.

Examples of the above transparent or semitransparent electrode material include a conductive metal oxide film and a semitransparent metal thin film. Specifically, films fabricated using conductive materials of indium oxide, zinc oxide, tin oxide, and composites thereof, indium tin oxide (ITO) and indium zinc oxide, and the like (NESA and the like), as well as gold, platinum, silver, copper, and the like are used. ITO, indium zinc oxide, and tin oxide are preferred. Examples of the method for fabricating the electrode include vacuum deposition, sputtering, ion plating, and plating. Also, organic transparent conductive films of polyaniline and its derivatives, polythiophene and its derivatives, and the like may be used as the electrode material. Further, metal, a conductive polymer, and the like can be used as the electrode material, and preferably, one electrode of the pair of electrodes is preferably a material having a small work function. For example, metal, such as lithium, sodium, potassium, rubidium, cesium, magnesium, calcium, strontium, barium, aluminum, scandium, vanadium, zinc, yttrium, indium, cerium, samarium, europium, terbium, and ytterbium, and alloys of two or more thereof, or alloys of one or more thereof and one or more of gold, silver, platinum, copper, manganese, titanium, cobalt, nickel, tungsten, and tin, graphite or graphite intercalation compounds, and the like are used.

Examples of the alloys include a magnesium-silver alloy, a magnesium-indium alloy, a magnesium-aluminum alloy, an indium-silver alloy, a lithium-aluminum alloy, a lithium-magnesium alloy, a lithium-indium alloy, and a calcium-aluminum alloy.

As the material used as a buffer layer as an additional layer, alkali metal, such as lithium fluoride, alkaline earth metal halide and oxide, and the like can be used. Also, fine particles of an inorganic semiconductor, such as titanium oxide, can be used.

<Method for Manufacturing Organic Thin Film>

The method for manufacturing the above organic thin film is not particularly limited, and includes, for example, a method of film formation from a solution comprising the fullerene derivative used in the present invention.

The solvent used for film formation from a solution is not particularly limited as long as the fullerene derivative used in the present invention is dissolved. Examples of this solvent include hydrocarbon solvents, such as toluene, xylene, mesitylene, tetralin, decalin, bicyclohexyl, n-butylbenzene, s-butylbenzene, and t-butylbenzene, halogenated saturated hydrocarbon solvents, such as carbon tetrachloride, chloroform, dichloromethane, dichloroethane, chlorobutane, bromobutane, chloropentane, bromopentane, chlorohexane, bromohexane, chlorocyclohexane, and bromocyclohexane, halogenated unsaturated hydrocarbon solvents, such as chlorobenzene, dichlorobenzene, and trichlorobenzene, and ether solvents, such as tetrahydrofuran and tetrahydropyran. Generally, 0.1 wt % or more of the above fullerene derivative can be dissolved in the above solvent.

The above solution may further comprise a polymer compound. Specific examples of the solvent used in the solution include the above-described solvents, but in terms of the solubility of the polymer compound, aromatic hydrocarbon solvents are preferred, and toluene, xylene, and mesitylene are more preferred.

For film formation from a solution, coating methods, such as spin coating, casting, microgravure coating, gravure coating, bar coating, roll coating, wire bar coating, dip coating, spray coating, screen printing, flexographic printing, offset printing, ink jet printing, dispenser printing, nozzle coating, and capillary coating, can be used, and spin coating, flexographic printing, ink jet printing, and dispenser printing are preferred.

In the organic photoelectric conversion device, by allowing light, such as sunlight, to enter from the transparent or semitransparent electrode, photoelectromotive force is generated between the electrodes, thereby, the organic photoelectric conversion device can be operated as an organic thin film solar cell. By integrating a plurality of organic thin film solar cells, they can also be used as an organic thin film solar cell module.

Also, by allowing light to enter from the transparent or semitransparent electrode, with voltage applied between the electrodes, light current flows, thereby, the organic photoelectric conversion device can be operated as an organic optical sensor. By integrating a plurality of organic optical sensors, they can also be used as an organic image sensor.

<Fullerene Derivative>

The fullerene derivative of the present invention is represented by the above formula (4). In the above formula (4), T is a group represented by the above formula (5) or (6). The fullerene derivative has excellent solubility in organic solvents, particularly, aromatic hydrocarbon solvents, such as toluene, xylene, and mesitylene.

When the fullerene derivative of the present invention has a group represented by the above formula (5), $R^3$ in the above formula (5) represents a halogen atom, an alkyl group, an alkoxy group, or an aryl group. A hydrogen atom included in these groups may be replaced by a halogen atom. When there is a plurality of $R^3$, the $R^3$ may be the same or different.

The alkyl group represented by $R^3$ in the above formula (5) generally has 1 to 20 carbon atoms and includes the same groups as the alkyl groups described for the above-described $R^1$.

The alkoxy group represented by $R^3$ in the above formula (5) generally has 1 to 20 carbon atoms and includes the same groups as the alkoxy groups described for the above-described $R^1$.

The aryl group represented by $R^3$ in the above formula (5) generally has 6 to 60 carbon atoms and may have a substituent. Examples of the aryl group include the same groups as the aryl groups described for the above-described $R^1$.

Examples of the halogen atom represented by $R^3$ in the above formula (5) include a fluorine atom, a chlorine atom, a bromine atom, and an iodine atom. In terms of conversion efficiency when the fullerene derivative is used in the organic photoelectric conversion device, a fluorine atom is preferred.

In the above formula (4), c represents an integer of 1 to 6. When there is a plurality of c, the c may be the same or different. In terms of the ease of availability of the raw materials, 2 is preferred. d represents an integer of 0 to 5. In terms of charge transport properties, 0 to 3 are preferred. e represents an integer of 1 to 4, and f represents an integer of 0 to 4.

In the above formula (5), g represents an integer of 0 to 7.

Among the fullerene derivatives having a group represented by the above formula (5), fullerene derivatives represented by the following formula (12) are preferred in terms of conversion efficiency when the fullerene derivative is used in the organic photoelectric conversion device.

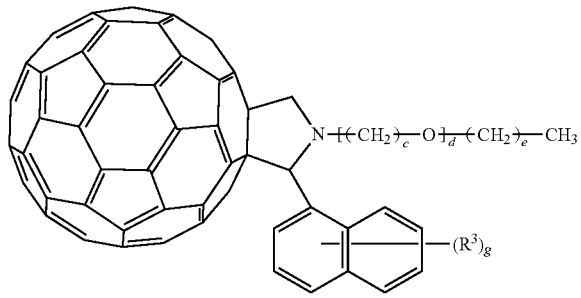

(12)

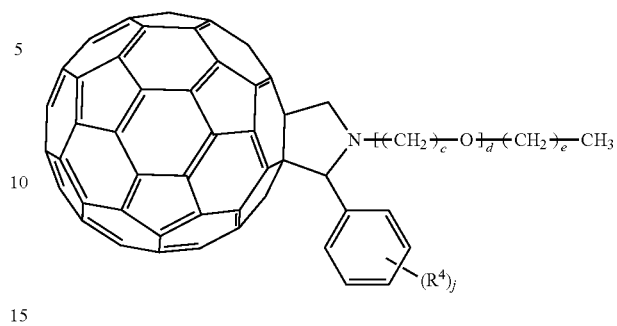

(13)

wherein $R^3$, c, d, e, and g represent the same meanings as described above.

In the above formula (12), c is preferably 2, d is preferably 2, e is preferably 0, and g is preferably 0 or 1, in terms of conversion efficiency when the fullerene derivative is used in the organic photoelectric conversion device. $R^3$ is preferably a fluorine atom or an alkyl group having 1 to 4 carbon atoms. The alkyl group may be substituted with a fluorine atom.

When the fullerene derivative of the present invention has a group represented by the above formula (6), $R^4$ in the above formula (6) represents a halogen atom, an alkyl group, an alkoxy group, or an aryl group. A hydrogen atom included in these groups may be replaced by a fluorine atom. When there is a plurality of $R^4$, the $R^4$ may be the same or different.

The alkyl group represented by $R^4$ in the above formula (6) generally has 1 to 20 carbon atoms and includes the same groups as the alkyl groups described for the above-described $R^1$.

The alkoxy group represented by $R^4$ in the above formula (6) generally has 1 to 20 carbon atoms and includes the same groups as the alkoxy groups described for the above-described $R^1$.

The aryl group represented by $R^4$ in the above formula (6) generally has 6 to 60 carbon atoms and may have a substituent. Examples of the aryl group include the same groups as the aryl groups described for the above-described $R^1$.

Examples of the halogen atom represented by $R^4$ in the above formula (6) include a fluorine atom, a chlorine atom, a bromine atom, and an iodine atom. In terms of conversion efficiency when the fullerene derivative is used in the organic photoelectric conversion device, a fluorine atom is preferred.

In the above formula (6), h represents an integer of 0 to 5, provided that when h is 0, f is an integer of 1 to 4. In terms of conversion efficiency when the fullerene derivative is used in the organic photoelectric conversion device, h is preferably 0 or 1.

Among the fullerene derivatives having a group represented by the above formula (6), fullerene derivatives represented by the following formula (13) are preferred in terms of solubility in organic solvents.

wherein j represents an integer of 1 to 4; and $R^4$, c, d, and e represent the same meanings as described above.

In the above formula (13), c is preferably 2, d is preferably 2, e is preferably 0, and j is preferably 1, in terms of conversion efficiency when the fullerene derivative is used in the organic photoelectric conversion device. $R^4$ is preferably a halogen atom or an alkyl group.

Among the fullerene derivatives represented by the above formula (13), fullerene derivatives represented by the following formula (14) are preferred in terms of conversion efficiency when the fullerene derivative is used in the organic photoelectric conversion device.

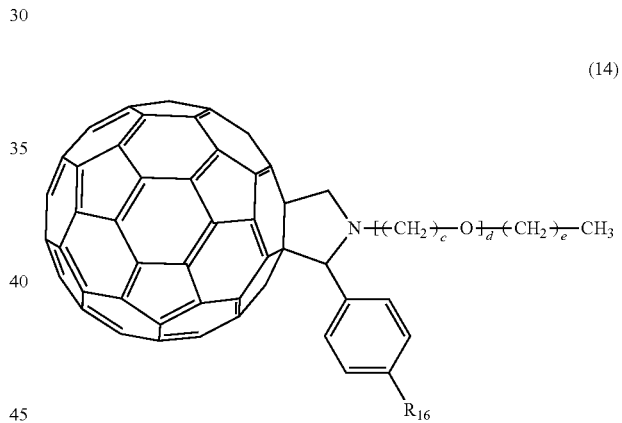

(14)

wherein c, d, and e represent the same meanings as described above; and $R^{16}$ represents a fluorine atom or an alkyl group having 1 to 4 carbon atoms.

EXAMPLES

Examples will be illustrated below for describing the present invention in more detail, but the present invention is not limited to these.

For reagents and solvents used in synthesis, commercial products were used as they were, or products, which were distilled and purified in the presence of a desiccant, were used. For $C_{60}$ fullerene, one manufactured by Frontier Carbon Corporation was used. NMR spectra were measured using MH500 manufactured by JEOL, and tetramethylsilane (TMS) was used as the internal standard. Infrared absorption spectra were measured using FR-IR 8000 manufactured by SHIMADZU CORPORATION. MALDI-TOF MS spectra were measured using AutoFLEX-T2 manufactured by BRUKER.

Example 1

Synthesis of Fullerene Derivative A

Synthesis of Benzyl(2-(2-hydroxyethoxy)ethylamino)acetate

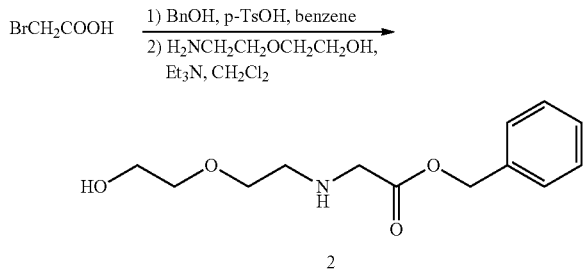

(First Step) Bromoacetic acid (20.8 g, 150 mmol), benzyl alcohol (16.2 g, 150 mmol), para-toluenesulfonic acid (258 mg, 1.5 mmol), and benzene (300 mL) were added to a two-necked flask equipped with a Dean-Stark trap and were subjected to dehydration condensation at 120° C. for 24 hours. The solvent was evaporated under reduced pressure by an evaporator, and then, the residue was purified by silica gel flash column chromatography (hexane/ethyl acetate=10/1, 5/1) to quantitatively obtain bromoacetic acid benzyl ester (34.3 g, 150 mmol) as a yellow oily material. $R_f$ 0.71 (hexane/ethyl acetate=4/1); $^1$H NMR (500 MHz, ppm, CDCl$_3$, J=Hz) δ 3.81 (s, 2H), 5.14 (s, 2H), 7.31 (s, 5H); $^{13}$C NMR (125 MHz, ppm, CDCl$_3$) δ 25.74, 67.79, 128.27, 128.48, 128.54, 134.88, 166.91; IR (neat, cm$^{-1}$) 2959, 1751, 1458, 1412, 1377, 1167, 972, 750, 698.

(Second Step) In an argon atmosphere, triethylamine (17 mL, 120 mmol) was added to a dichloromethane (90 mL) solution of bromoacetic acid benzyl ester (13.7 g, 60 mmol) at 0° C., and the obtained liquid mixture was stirred at the same temperature for 20 minutes. Then, a dichloromethane (40 mL) solution of 2-(2-aminoethoxy)ethanol (12 mL, 120 mmol) was added, and the mixture was stirred at room temperature for 4 hours. Then, the organic layer was washed with water (3 times), and then dried with anhydrous magnesium sulfate. The solvent was evaporated under reduced pressure by the evaporator, and then, the residue was purified by silica gel flash column chromatography (developing solvent=ethyl acetate/methanol=1/0, 10/1, 5/1) to obtain glycine ester 2 (12.2 g, 48.0 mmol) as a colorless oily material, with a yield of 80%.

$R_f$ 0.48 (ethyl acetate/methanol=2/1); $^1$H NMR (500 MHz, ppm, CDCl$_3$, J=Hz) δ 2.83 (t, 2H, J=5.1 Hz), 3.50 (s, 2H), 3.52 (t, 2H, J=4.6 Hz), 3.58 (t, 2H, J=5.0 Hz), 3.65 (t, 2H, J=4.6 Hz), 5.11 (s, 2H), 7.28-7.30 (m, 5H); $^{13}$C NMR (125 MHz, ppm, CDCl$_3$) δ 48.46, 50.25, 61.29, 66.38, 69.80, 72.23, 126.63, 128.12, 128.37, 135.30, 171.78; IR (neat, cm$^{-1}$) 3412, 2880, 1719, 1638, 1560, 1508, 1458, 1067, 669.

Synthesis of (2-(2-methoxyethoxy)ethylamino)acetic acid (1)

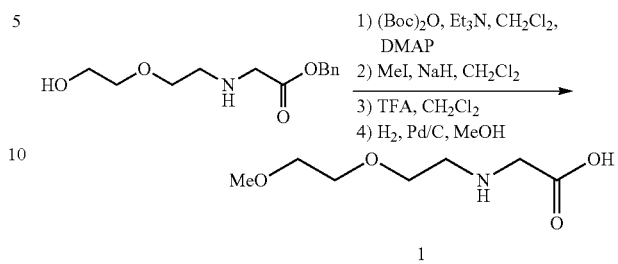
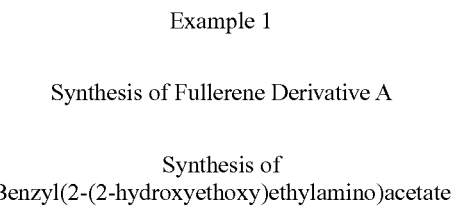

(First Step) In an argon atmosphere, triethylamine (4.3 mL, 31 mmol) was added to a dichloromethane (50 mL) solution of benzyl 2-(2-(2-hydroxyethoxy)ethylamino)acetate (2) (6.58 g, 26 mmol) at 0° C., and then, 4-(N,N-dimethylamino) pyridine (DMAP) (32 mg, 0.26 mmol) was added. The obtained liquid mixture was stirred for 20 minutes, and then, a dichloromethane (10 mL) solution of di-tert-butyl dicarbonate (6.77 g, 31 mmol) was dropped into the liquid mixture. The reaction liquid mixture was stirred at room temperature for 4 hours, and then poured into an Erlenmeyer flask containing water to stop reaction. Diethyl ether extraction (3 times) was performed. The organic layer was dried, then concentrated under reduced pressure, and then, purified by silica gel flash column chromatography (developing solvent: hexane/ethyl acetate=3/1, 2.5/1, 2/1) to obtain benzyl{tert-butoxycarbonyl [2-(2-hydroxy-ethoxy)ethyl]amino}acetate (5.83 g, 16.5 mmol) as a colorless oily material, with a yield of 63%.

$R_f$ 0.58 (ethyl acetate/methano=20/1); $^1$H NMR (500 MHz, ppm, CDCl$_3$, J=Hz) δ 1.34,(d, 9H, J=54.5 Hz), 2.19 (brs, 1H), 3.38-3.45 (m, 4H), 3.50-3.60 (m, 4H), 3.99 (d, 2H, J=41.3 Hz), 5.09 (d, 2H, J=4.1 Hz), 7.25-7.30 (m, 5H); $^{13}$C NMR (125 MHz, ppm, CDCl$_3$) δ 27.82, 28.05, 47.90, 48.20, 49.81, 50.39, 61.23, 66.42, 69.92, 72.12, 80.08, 127.93, 128.14, 135.25, 154.99, 155.19, 169.94, 170.07; IR (neat, cm$^{-1}$) 3449, 2934, 2872, 1751, 1701, 1458, 1400, 1367, 1252, 1143; $C_{18}H_{27}NO_6$Anal.: Calcd.: C, 61.17; H, 7.70; N, 3.96. Measured: C, 60.01; H, 7.75; N, 4.13.

(Second Step) In an argon gas atmosphere, a tetrahydrofuran (THF) (20 mL) solution of benzyl{tert-butoxycarbonyl [2-(2-hydroxy-ethoxy)ethyl]amino}acetate (5.83 g, 16.5 mmol) was dropped into a THF (10 mL) solution of sodium hydride (1.2 g, 24.8 mmol, 50% in mineral oil) at 0° C., and the mixture was stirred at the same temperature for 20 minutes. Then, iodomethane (1.6 mL, 24.8 mmol) was added at 0° C. The reaction liquid mixture was stirred at room temperature for 20 hours, and then, water was added, while the reaction liquid mixture was cooled in an ice bath, to stop reaction. Ether extraction (3 times) was performed. The organic layer was dried, then concentrated under reduced pressure, and purified by silica gel flash column chromatography (developing solvent: hexane/ethyl acetate =5/1, 3/1) to obtain benzyl{tert-butoxycarbonyl-[2-(2-methoxy-ethoxy) ethyl]amino}acetate (3.02 g, 8.21 mmol) as a colorless oily material, with a yield of 50%.

$R_f$ 0.54 (hexane/ethyl acetate=1/1); $^1$H NMR (500 MHz, ppm, CDCl$_3$, J=Hz) δ1.34 (d, 9H, J=51.8 Hz), 3.28 (d, 3H, J=2.7 Hz), 3.37-3.46 (m, 6H), 3.52 (dt, 2H, J=5.4 Hz, 16.5 Hz), 4.02 (d, 2H, J=34.8 Hz), 5.09 (d, 2H, J=4.5 Hz), 7.24-7.30 (m, 5H); $^{13}$C NMR (125 MHz, ppm, CDCl$_3$) δ24.93, 25.16, 44.68, 45.00, 46.70, 47.40, 55.78, 63.30, 67.22, 68.60, 76.95, 124.98, 125.14, 125.36, 132.49, 151.99, 152.31, 166.84, 166.96; IR (neat, cm$^{-1}$) 2880, 1751, 1701, 1560, 1458, 1400, 1366, 1117, 698, 617; $C_{19}H_{29}NO_6$ Anal.: Calcd.: C, 62.11; H, 7.96; N, 3.81. Measured: C, 62.15; H, 8.16; N, 3.83.

(Third Step) In an argon atmosphere, trifluoroacetic acid (TFA) (9.0 mL) was added to a dichloromethane (17 mL) solution of benzyl {tert-butoxycarbonyl-[2-(2-methoxyethoxy)ethyl]amino} acetate (3.02 g, 8.21 mmol), and the mixture was stirred at room temperature for 7 hours. Then, 10% sodium carbonate aqueous solution was added to adjust to pH 10, and dichloromethane extraction was performed. The organic layer was dried with anhydrous magnesium sulfate and concentrated under reduced pressure to quantitatively obtain benzyl[2-(2-methoxy-ethoxy)ethylamino]acetate (2.18 g, 8.19 mmol) as a yellow oily material.

$R_f$ 0.32 (ethyl acetate/methano=20/1); $^1$H NMR (500 MHz, ppm, CDCl$_3$, J=Hz) δ1.99 (brs, 1H), 2.83 (t, 2H, J=5.3 Hz), 3.38 (s, 3H), 3.50 (s, 2H), 3.54 (t, 2H, J=4.6 Hz), 3.60-3.62 (m, 4H), 5.17(s, 2H), 7.32-7.38 (m, 5H); $^{13}$C NMR (125 MHz, ppm, CDCl$_3$) δ48.46, 50.66, 58.76, 66.20, 70.00, 70.44, 71.64, 128.09, 128.33, 135.44, 171.84; IR (neat, cm$^{-1}$) 3350, 2876, 1736, 1560, 1458, 1117, 1030, 698, 619; $C_{14}H_{21}NO_4$ Anal.: Calcd.: C, 62.90; H, 7.92; N, 5.24. Measured: C, 62.28; H, 8.20; N, 5.05.

(Fourth Step) Activated carbon (219 mg) supporting 10 wt% palladium was added to a methanol (27 mL) solution of benzyl[2-(2-methoxy-ethoxy)ethylamino]acetate (2.19 g, 8.19 mmol) at room temperature. Hydrogen gas purging was performed, and then, in a hydrogen atmosphere, the mixture was stirred at room temperature for 7 hours. Pd/C were removed by a glass filter in which a celite pad was laid, and the celite layer was washed with methanol. The filtrate was concentrated under reduced pressure to obtain [2-(2-methoxyethoxy)ethylamino]acetic acid (1) (1.38 g, 7.78 mmol) as a yellow oily material, with a yield of 95%.

$^1$H NMR (500 MHz, ppm, MeOD, J=Hz) δ3.21 (t, 2H, J=5.1 Hz), 3.38 (s, 3H), 3.51 (s, 2H), 3.57 (t, 2H, J=4.4 Hz), 3.65 (t, 2H, J=4.6 Hz), 3.73 (t, 2H, J=5.1 Hz); $^{13}$C NMR (125 MHz, ppm, MeOD) δ48.13, 50.49, 59.16, 67.08, 71.05, 72.85, 171.10; IR (neat, cm$^{-1}$) 3414, 2827, 1751, 1630, 1369, 1111, 1028, 851, 799; $C_7H_{15}NO_4$ Anal.: Calcd.: C, 47.45; H, 8.53; N, 7.90. Measured: C, 46.20; H, 8.49; N, 7.43.

Synthesis of N-methoxyethoxyethyl-2-(1-naphthyl) fulleropyrrolidine (Fullerene Derivative A)

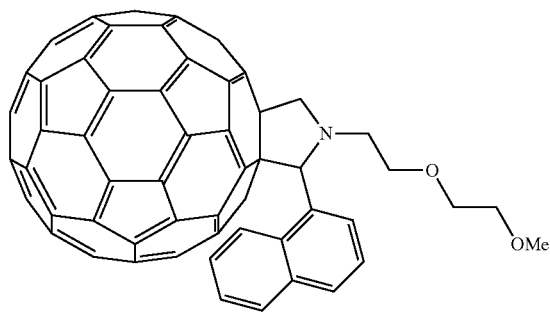

(A)

A fullerene derivative A was synthesized by the 1,3-dipolar cycloaddition reaction of fullerene and iminium cations produced by the decarboxylation of imine produced from a glycine derivative 1 and 1-naphthoaldehyde (Prato reaction).

In an argon atmosphere generated in a system, $C_{60}$ (500 mg, 0.69 mmol), the glycine derivative 1 (185 mg, 1.04 mmol), 1-naphthylaldehyde (217 mg, 1.39 mmol), and chlorobenzene (100 mL) were mixed in a three-neck flask equipped with a Dimroth condenser, and heated to reflux at 150° C. for 3 hours. The mixture was allowed to cool to room temperature, and the solvent was evaporated under reduced pressure by a rotary evaporator. The obtained solids were separated and purified by silica gel flash column chromatography (developing solvent: carbon disulfide/ethyl acetate=1/0 to 20/1) to obtain the target fullerene derivative A (356 mg, 0.36 mmol, yield: 52%) as a brown powder. The obtained powder was washed with methanol five times, and then dried under reduced pressure.

$^1$H NMR (500 MHz, ppm, CDCl$_3$, J=Hz) δ 2.89-2.94 (1H, m), 3.43 (3H, s), 3.43-3.50 (1H, m), 3.62-3.65 (2H, m), 3.76-3.78 (2H, m), 3.96-4.00 (1H, m), 4.05-4.10 (1H, m), 4.49 (1H, d, J=10.0 Hz), 5.31 (1H, d, J=10.0 Hz), 6.16 (1H, s), 7.44-7.45 (2H, m), 7.62 (1H, t, J=8.0 Hz), 7.83 (1H, d, J=9.0 Hz), 7.87 (1H, d, J=8.0 Hz), 8.39 (1H, d, J=6.0 Hz), 8.52 (1H, d, J=8.0 Hz); $^{13}$C NMR (125 MHz, ppm, CDCl$_3$) δ 51.98, 59.19, 67.71, 69.50, 70.51, 72.04, 76.29, 123.91, 125.52, 125.81, 126.11, 128.07, 128.63, 129.16, 132.65, 133.19, 133.99, 135.47, 135.87, 136.13, 136.66, 139.26, 139.49, 140.14, 140.34, 141.56, 141.64, 141.77, 141.97, 142.04, 142.11, 142.24, 142.27, 142.30, 142.56, 142.66, 142.93, 143.10, 144.23, 144.39, 144.57, 144.64, 145.09, 145.20, 145.25, 145.29, 145.44, 145.55, 145.68, 145.74, 145.92, 146.07, 146.20, 146.73, 147.04, 147.25, 147.31, 153.70, 154.17, 154.26, 156.81; IR (KBr, cm$^{-1}$) 2808, 1508, 1456, 1425, 1178, 1107, 773, 527; MALDI-TOF-MS (matrix: SA) Measured 991.203 (exact mass calculated for $C_{77}H_{21}NO_2$: 991.173).

Example 2

Synthesis of N-methoxyethoxyethyl-2-(perfluorophenyl)fulleropyrrolidine (Fullerene Derivative B)

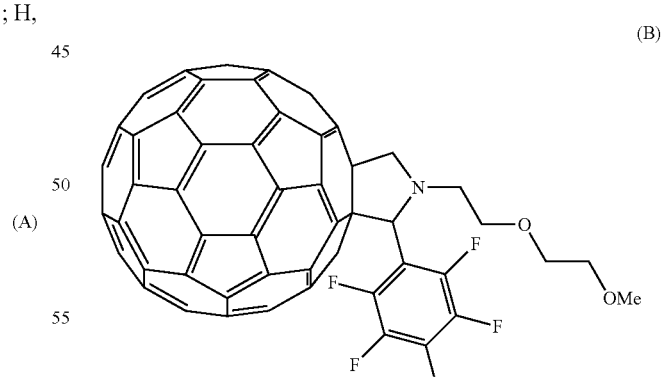

(B)

Fullerene $C_{60}$ (250 mg, 0.35 mmol), the glycine derivative 1 (92 mg, 0.52 mmol), and pentafluorobenzaldehyde (136 mg, 0.69 mmol) in 50 mL of chlorobenzene were heated to reflux for 2 hours, and purification was performed by operation similar to that of Example 1 to obtain 179 mg (0.17 mmol, yield 50%) of a fullerene derivative B.

$^1$H NMR (500 MHz, ppm, CDCl$_3$, J=Hz) δ 3.08-3.14 (1H, m), 3.37-3.42 (1H, m), 3.45 (3H, s), 3.65-3.68 (2H, m), 3.80-

3.82 (2H, m), 3.95-3.99 (1H, m), 4.12-4.17 (1H, m), 4.35 (1H, dd, J=10.0 Hz, 3.0 Hz), 5.18 (1H, d, J=19.0 Hz), 5.79 (1H, s); $^{13}$C NMR (125 MHz, ppm, CDCl$_3$) δ 51.85, 58.70, 66.68, 69.06, 69.57, 70.59, 71.90, 72.86, 72.89, 74.57, 125.13, 128.03, 128.77, 135.26, 135.63, 136.37, 137.82, 139.33, 139.97, 140.00, 140.04, 141.37, 141.41, 141.44, 141.67, 141.69, 141.83, 141.90, 141.99, 142.38, 142.47, 142.81, 142.87, 144.05, 144.17, 144.24, 144.49, 144.96, 145.02, 145.10, 145.13, 145.18, 145.28, 145.32, 145.41, 145.73, 145.83, 145.86, 145.94, 146.06, 146.09, 147.06, 147.08, 150.76, 152.02, 153.14, 155.40; $^{19}$F NMR (470 MHz, ppm, CDCl$_3$, J=Hz) δ 9.24 (1F, d, J=23.0 Hz), 21.68 (2F, d, J=23.0 Hz), 28.48 (2F, d, J=17.0 Hz); IR (Neat, cm$^{-3}$) 2873, 1523, 1501, 1107, 997, 754, 527; MALDI-TOF-MS (neat) Measured 1031.234 (exact mass calculated for C73H14F5NO2: 1031.094).

Example 3

Synthesis of N-methoxyethoxyethyl-2-(4-fluorophenyl)fulleropyrrolidine (Fullerene Derivative C)

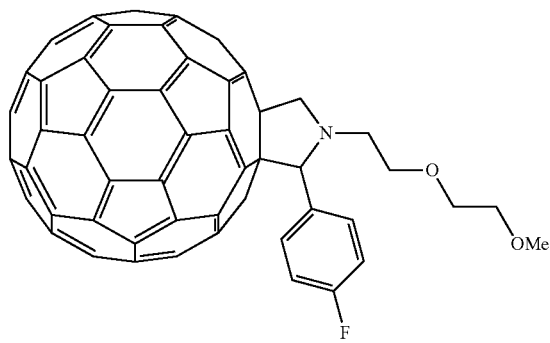

(C)

Fullerene C$_{60}$ (250 mg, 0.35 mmol), the glycine derivative 1 (92 mg, 0.52 mmol), and 4-fluorobenzaldehyde (86 mg, 0.69 mmol) in 50 mL of chlorobenzene were heated to reflux for 2 hours. Purification was performed by operation similar to that of Example 1 to obtain 192 mg (0.20 mmol, yield: 58%) of a fullerene derivative C.

$^1$H NMR (500 MHz, ppm, CDCl$_3$, J=Hz) δ 2.82-2.85 (1H, m), 3.37 (3H, s), 3.59-3.61 (2H, m), 3.71-3.74 (2H, m), 3.92-3.94 (1H, m), 3.97-4.00 (1H, m), 4.27 (1H, d, J=19.0 Hz), 5.19 (1H, s), 5.20 (1H, d, J=19.0 Hz), 7.04 (2H, t, J=17.0 Hz), 7.75 (2H, br); $^{13}$C NMR (125 MHz, ppm, CDCl$_3$) δ 52.01, 59.19, 67.63, 69.11, 70.41, 70.59, 72.07, 76.21, 81.62, 115.59, 115.74, 131.03, 131.09, 132.98, 135.63, 135.90, 136.45, 136.91, 139.47, 139.90, 140.14, 140.19, 141.53, 141.68, 141.82, 141.87, 141.98, 142.02, 142.05, 142.10, 142.13, 142.17, 142.27, 142.55, 142.57, 142.69, 143.00, 143.17, 144.36, 144.42, 144.59, 144.72, 145.15, 145.21, 145.26, 145.33, 145.52, 145.72, 145.94, 145.95, 146.04, 146.11, 146.14, 146.17, 146.21, 146.28, 146.30, 146.46, 146.61, 147.32, 153.16, 153.29, 154.13, 156.47, 161.72; $^{19}$F NMR (470 MHz, ppm, CDCl$_3$) δ 49.55 (1F, s); IR (neat, cm$^{-1}$) 2880, 1508, 1225, 1109, 754, 527; MALDI-TOF-MS (matrix: SA) Measured 958.476 (exact mass calculated for C73H18FNO2: 959.132).

Example 4

Synthesis of N-methoxyethoxyethyl-2-(4-methylphenyl)fulleropyrrolidine (Fullerene Derivative D)

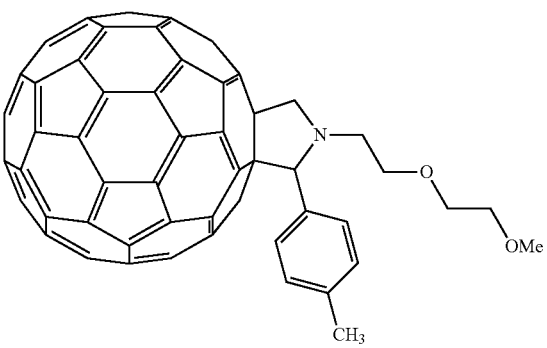

(D)

Fullerene C$_{60}$ (250 mg, 0.35 mmol), the glycine derivative 1 (92 mg, 0.52 mmol), and 4-fluorobenzaldehyde (83 mg, 0.69 mmol) in 50 mL of chlorobenzene were heated to reflux for 2 hours. Purification was performed by operation similar to that of Example 1 to obtain 133 mg (0.14 mmol, yield: 40%) of a fullerene derivative D.

Synthesis Example 1

Synthesis of N-methoxyethoxyethyl-2-phenyl-fulleropyrrolidine (Fullerene Derivative E)

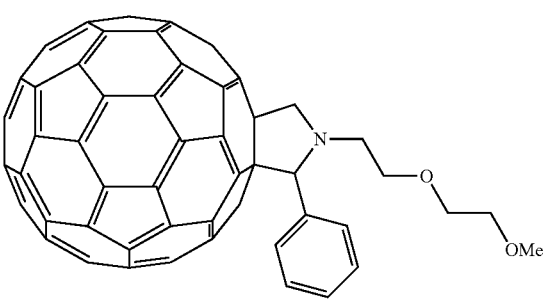

(E)

Fullerene C$_{60}$ (250 mg, 0.35 mmol), the glycine derivative 1 (92 mg, 0.52 mmol), and 4-fluorobenzaldehyde (83 mg, 0.69 mmol) in 50 mL of chlorobenzene were heated to reflux for 2 hours. Purification was performed by operation similar to that of Example 1 to obtain 133 mg (0.14 mmol, yield: 40%) of a fullerene derivative E.

Example 5

Synthesis of Fullerene Derivative F

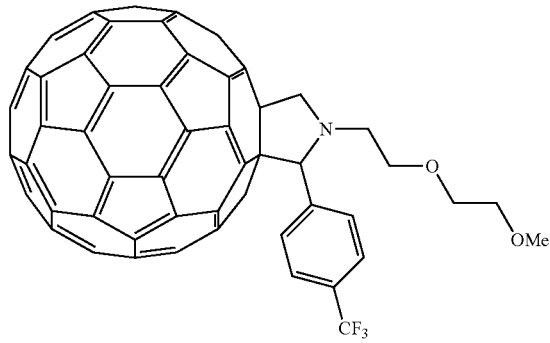

(F)

Fullerene $C_{60}$ (250 mg, 0.35 mmol), the glycine derivative 1 (92 mg, 0.52 mmol), and 4-trifluoromethylbenzaldehyde (121 mg, 0.69 mmol) in 50 mL of chlorobenzene were heated to reflux for 2 hours. Purification was performed by operation similar to that of Example 1 to obtain 170 mg (0.17 mmol, yield: 49%) of a fullerene derivative F.

Example 6

Synthesis of N-methoxyethoxyethyl-2-(2-phenyl-ethyl)fulleropyrrolidine (Fullerene Derivative G)

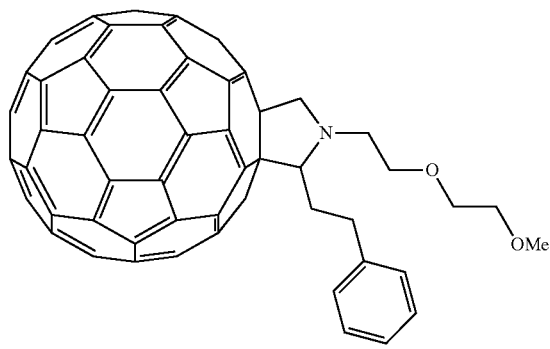

(G)

Fullerene $C_{60}$ (250 mg, 0.35 mmol), the glycine derivative 1 (92 mg, 0.52 mmol), and 3-phenylpropionaldehyde (93 mg, 0.69 mmol) in 50 mL of chlorobenzene were heated to reflux for 2 hours. Purification was performed by operation similar to that of Example 1 to obtain 164 mg (0.17 mmol, yield: 48%) of a fullerene derivative G.

Example 7

Synthesis of N-methoxyethoxyethyl-2-(2-naphthyl)fulleropyrrolidine (Fullerene Derivative H)

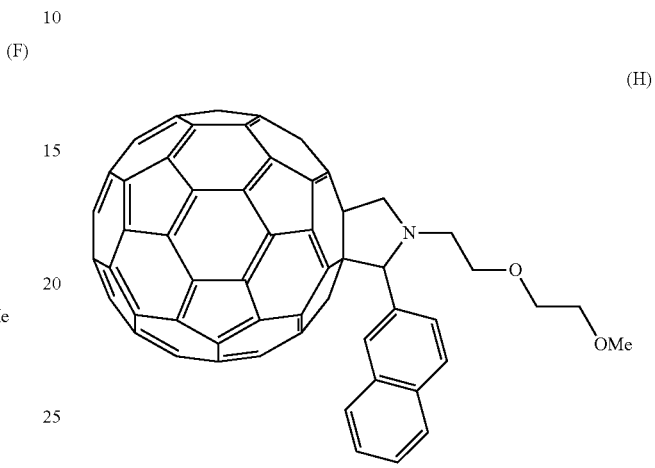

(H)

Fullerene $O_{60}$ (500 mg, 0.69 mmol), the glycine derivative 1 (185 mg, 1.04 mmol), and 2-naphthoaldehyde (217 mg, 1.39 mmol) in 100 mL of chlorobenzene were heated to reflux for 3 hours. Purification was performed by operation similar to that of Example 1 to obtain 262 mg (0.26 mmol, yield: 38%) of a fullerene derivative H.

$^1$H NMR (500 MHz, ppm, CDCl$_3$, J=Hz) δ 2.90-2.95 (1H, m), 3.44 (3H, s), 3.65-3.67 (2H, m), 3.76-3.80 (2H, m), 3.97-4.02 (1H, m), 4.05-4.10 (1H, m), 4.36 (1H, d, J=19.0 Hz), 5.26 (1H, d, J=20.0 Hz), 5.34 (1H, s), 7.47-7.49 (3H, m), 7.83-7.90 (4H, m); $^{13}$C NMR (125 MHz, ppm, CDCl$_3$) δ 52.12, 59.17, 67.73, 69.38, 70.49, 72.06, 76.39, 126.18, 126.25, 127.79, 128.09, 128.50, 133.47, 134.81, 135.66, 136.56, 136.92, 139.48, 139.87, 140.14, 141.47, 141.67, 141.75, 141.86, 141.92, 142.01, 142.64, 142.11, 142.14, 142.28, 142.48, 142.52, 142.65, 142.97, 143.11, 144.36, 144.39, 144.54, 144.70, 145.12, 145.17, 145.23, 145.32, 145.51, 145.55, 145.58, 145.73, 145.90, 146.10, 146.14, 146.19, 146.29, 146.48, 146.78, 147.27, 153.32, 153.57, 154.38, 156.51; IR (neat, cm$^{-1}$) 2922, 1215, 1184, 1109, 752, 669, 527; MALDI-TOF-MS (matrix: SA) Measured 990.629 (exact mass calculated for C$_{77}$H$_{21}$NO$_2$: 991.173).

Evaluation Examples 1 to 8

Evaluation of Solubility in Xylene

A xylene solvent was added to a fullerene derivative shown in Table 1 at a concentration of 1 wt %, and the mixture was stirred by a magnetic stirrer for 10 minutes. The subsequent solubility in xylene solvent was visually observed. The results are shown in Table 1.

TABLE 1

| | Fullerene derivative | Solubility of a 1 wt % xylene solution |
|---|---|---|
| Evaluation Example 1 | A | Dissolved |
| Evaluation Example 2 | B | Dissolved |
| Evaluation Example 3 | C | Dissolved |
| Evaluation Example 4 | D | Dissolved |
| Evaluation Example 5 | E | Dissolved |
| Evaluation Example 6 | F | Dissolved |
| Evaluation Example 7 | G | Dissolved |
| Evaluation Example 8 | [60] PCBM | Insoluble matter is present |

(Fabrication and Evaluation of Organic Thin Film Solar Cell)

Regioregular poly(3-hexylthiophene) (manufactured by Aldrich, lot number: 15409BE, Mw=41000, Mn=22000) as an electron donor was dissolved in o-dichlorobenzene at a concentration of 1% (wt %). Then, a fullerene derivative shown in Table 2 was mixed in the solution as an electron acceptor having a weight equal to the weight of the electron donor. Then, the mixture was filtered by a 1.0 μm Teflon (registered trademark) filter to make a coating solution.

A glass substrate on which an ITO film with a thickness of 150 nm was provided by sputtering was subjected to ozone-UV treatment for surface treatment. Next, the substrate was coated with the above coating solution by spin coating to obtain the activity layer (film thickness: about 100 nm) of an organic thin film solar cell. Then, the substrate was baked under conditions of 90° C. in a vacuum for 60 minutes. Then, lithium fluoride with a thickness of 4 nm was vapor-deposited by a vacuum deposition machine, and then, Al with a thickness of 100 nm was vapor-deposited. The degree of vacuum during vapor deposition was 1 to $9\times10^{-3}$ Pa for all. The shape of the obtained organic thin film solar cell was a 2 mm×2 mm square. The photoelectric conversion efficiency of the obtained organic thin film solar cell was obtained by emitting constant light using a solar simulator (manufactured by Bunkoukeiki Co., LTD., trade name: OTENTO-SUNII: AM1.5G filter, irradiance: 100 mW/cm$^2$), and measuring generated current and voltage. The results are shown in Table 2.

TABLE 2

| | Fullerene derivative | Photoelectric conversion efficiency (%) |
|---|---|---|
| Example 8 | A | 2.6 |
| Example 9 | C | 2.7 |
| Example 10 | D | 2.7 |
| Example 11 | E | 2.6 |
| Example 12 | H | 2.6 |
| Comparative Example 1 | [60] PCBM | 2.3 |

[60] PCBM (Phenyl C61-butyric acid methyl ester, manufactured by Frontier Carbon Corporation, trade name: E100)

Example 13

Synthesis of N-methoxyethoxyethyl-2-(4-biphenyl)fulleropyrrolidine (Fullerene Derivative I)

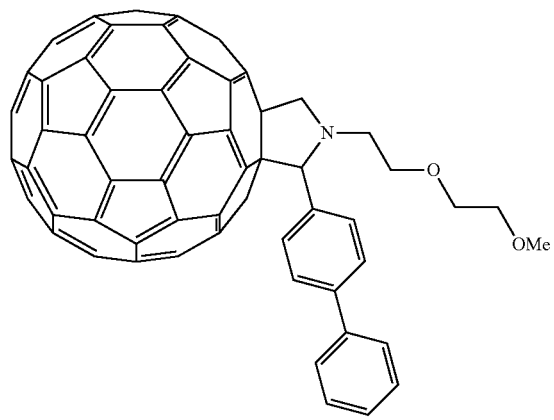

(I)

Fullerene $C_{60}$ (250 mg, 0.35 mmol), the glycine derivative 1 (92 mg, 0.52 mmol), and biphenyl-4-carboxaldehyde (126 mg, 0.69 mmol) were placed in a two-neck flask (100 mL) equipped with a Dimroth condenser, and chlorobenzene (50 mL) was added. The mixture was heated to reflux for 3 hours. The mixture was allowed to cool to room temperature, and then, the solvent was removed by the rotary evaporator. Then, the residue was purified using silica gel flash column chromatography (developing solvent: carbon disulfide/ethyl acetate=1/0 to 20/1) to obtain 150 mg (0.15 mmol, 42%) of a fullerene derivative I (brown powder). This powder was washed with methanol five times, and then dried under reduced pressure.

$^1$H NMR (400 MHz, ppm, CDCl$_3$, J=Hz) δ 2.84-2.90 (1H, m), 3.36-3.48 (2H, m), 3.40 (3H, s), 3.57-3.66 (2H, m), 3.71-3.80 (2H, m), 3.93-3.98 (1H, m), 4.00-4.06 (1H, m), 4.29 (1H, d, J=9.5 Hz), 5.17 (1H, s), 5.22 (1H, d, J=9.9 Hz), 7.26 (1H, dt, $J_1$=1.1 Hz, $J_2$=7.7 Hz), 7.35 (2H, dd, $J_1$=8.4 Hz, $J_2$=7.0 Hz), 7.52 (2H, dd, $J_1$=1.1 Hz, $J_2$=8.2 Hz), 7.58 (2H, d, J=8.4 Hz), 7.82 (d, 2H, J=7.82 Hz); $^{13}$C NMR (100 MHz, ppm, CDCl$_3$) δ 41.83, 48.49, 57.29, 58.66, 60.22, 61.67, 65.70, 71.72, 116.45, 116.51, 116.82, 116.92, 117.73, 118.29, 118.49, 119.39, 125.12, 125.58, 126.01, 126.38, 129.02, 129.41, 129.61, 129.61, 129.86, 130.69, 130.99, 131.12, 131.35, 131.42, 131.47, 131.52, 131.60, 131.73, 132.01, 132.44, 132.59, 133.80, 133.84, 134.07, 134.15, 134.56, 134.63, 134.68, 134.74, 134.81, 134.94, 135.01, 135.20, 135.35, 135.52, 135.55, 135.60, 135.63, 135.70, 135.70, 135.75, 135.89, 136.21, 136.70, 142.74, 142.90, 143.63, 145.88; IR (KBr, cm$^{-1}$) 3435, 2864, 2803, 1485, 1462, 1427, 1337, 1304, 1179, 1107, 1007, 843, 762, 694, 527; MALDI-TOF-MS (matrix: SA) Measured 1016.3050 (exact mass calculated for $C_{79}H_{23}NO_2^+$: 1017.1729).

Example 14

Synthesis of N-methoxyethoxyethyl-2-(4-methoxyphenyl)fulleropyrrolidine (Fullerene Derivative J)

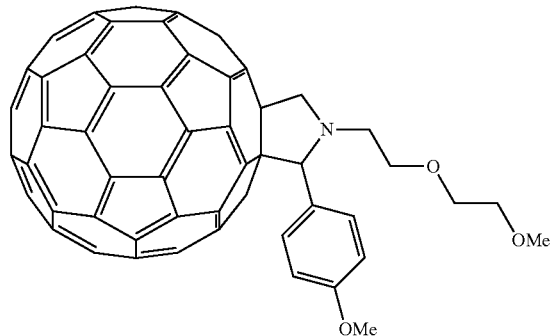

(J)

100 mL of chlorobenzene was added to fullerene $C_{60}$ (500 mg, 0.69 mmol), the glycine derivative 1 (185 mg, 1.04 mmol), and 4-methoxybenzaldehyde (189 mg, 1.39 mmol), and the mixture was heated to reflux for 2 hours. The solvent was evaporated under reduced pressure, and then, the residue was purified using silica gel flash column chromatography (developing solvent: carbon disulfide/toluene/ethyl acetate=1/0/0 to 0/40/1) to obtain 312 mg (0.321 mmol, 42%) of a fullerene derivative J. This powder was washed with methanol five times, and then dried under reduced pressure.

$^1$H NMR (400 MHz, ppm, CDCl$_3$, J=Hz) δ 2.78-2.84 (1H, m), 3.39 (3H, s), 3.35-3.45 (1H, m), 3.56-3.63 (2H, m), 3.69-3.79 (2H, m), 3.75 (3H, s), 3.89-3.94 (1H, m), 3.96-4.02 (1H, m), 4.24 (1H, d, J=9.8 Hz), 5.06 (1H, s), 5.17 (1H, d, J=9.7 Hz), 6.86 (2H, d, J=8.3 Hz), 7.64 (2H, d, J=6.9 Hz); $^{13}$C NMR (100 MHz, ppm, CDCl$_3$) δ 51.99, 54.62, 58.74, 67.49, 68.77, 70.47, 70.52, 71.95, 76.14, 81.76, 113.84, 128.01, 128.62, 130.23, 135.41, 135.53, 136.28, 136.53, 139.25, 139.66, 139.84, 139.90, 141.24, 141.37, 141.52, 141.63, 141.68, 141.80, 141.83, 141.86, 141.99, 142.26, 142.29, 142.37, 142.70, 142.85, 144.07, 144.35, 144.41, 144.81, 144.89, 144.89, 144.99, 145.05, 145.19, 145.27, 145.47, 145.60, 145.76, 145.80, 145.84, 145.94, 145.99, 146.07, 146.21, 146.50, 146.96, 153.30, 153.35, 153.94, 156.28, 159.27; IR (KBr, cm$^{-1}$) 3460, 3893, 2866, 2828, 1609, 1508, 1456, 1429, 1302, 1246, 1180, 1171, 1107, 1034, 831, 573, 527; MALDI-TOF-MS (matrix: SA) Measured 971.1522 (exact mass calculated for C$_{74}$H$_{21}$NO$_3^+$: 971.1521).

Example 15

Synthesis of N-methoxyethoxyethyl-2-(4-chlorophenyl)fulleropyrrolidine (Fullerene Derivative K)

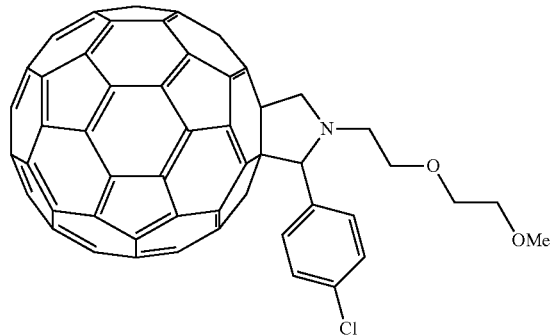

(K)

Fullerene $C_{60}$ (500 mg, 0.69 mmol), the glycine derivative 1 (184 mg, 1.04 mmol), and 4-chlorobenzaldehyde (196 mg, 1.39 mmol) were placed in a two-neck flask (200 mL) equipped with a Dimroth condenser, and chlorobenzene (100 mL) was added. The mixture was heated to reflux for 2 hours. The mixture was allowed to cool to room temperature, and then, the solvent was removed by the rotary evaporator. Then, the residue was purified using silica gel flash column chromatography (developing solvent: carbon disulfide/ethyl acetate=1/0 to 20/1) to obtain 254 mg (0.26 mmol, 38%) of a fullerene derivative K (brown powder). This powder was washed with methanol five times, and then dried under reduced pressure.

$^1$H NMR (500 MHz, ppm, CDCl$_3$, J=Hz) δ 2.85-2.90 (1H, m), 3.37-3.47 (1H, m), 3.42 (3H, s), 3.62-3.65 (2H, m), 3.71-3.80 (2H, m), 3.94-3.98 (1H, m), 4.01-4.05 (1H, m), 4.29 (1H, d, J=9.6 Hz), 5.14 (1H, s), 5.21 (1H, d, J=9.6 Hz), 7.37 (2H, d, J=8.8 Hz), 7.75 (2H, d, J=4.6 Hz); $^{13}$C NMR (100 MHz, ppm, CDCl$_3$) δ 52.02, 58.98, 67.51, 68.94, 70.34, 70.53, 71.98, 75.90, 81.52, 128.83, 130.58, 134.26, 135.48, 135.63, 135.79, 136.30, 136.83, 139.43, 139.81, 140.04, 140.07, 141.42, 141.55, 141.70, 141.83, 141.88, 141.93, 141.93, 141.98, 142.01, 142.11, 142.42, 142.55, 142.87, 142.87, 143.01, 144.20, 144.26, 144.45, 144.56, 145.01, 145.05, 145.05, 145.10, 145.14, 145.19, 145.29, 145.33, 145.40, 145.56, 145.81, 145.94, 145.99, 146.03, 146.06, 146.12, 146.16, 146.24, 146.39, 147.14, 152.71, 152.94, 153.84, 156.13; IR (KBr, cm$^{-1}$) 2862, 2803, 1489, 1458, 1420, 1180, 1107, 1090, 1015, 839, 829, 598, 573, 527; MALDI-TOF-MS (matrix: SA) Measured 975.1024 (exact mass calculated for C$_{73}$H$_{18}$ClNO$_2^+$: 975.1026)

(Fabrication and Evaluation of Organic Thin Film Solar Cell)

Regioregular poly(3-hexylthiophene) (manufactured by Aldrich, lot number: 01004AH, Mw=43000, Mn=22000) as an electron donor was dissolved in o-dichlorobenzene at a concentration of 1% (wt %). Then, a fullerene derivative shown in Table 3 was mixed in the solution as an electron acceptor having a weight equal to the weight of the electron donor. Then, the mixture was filtered by a Teflon (registered trademark) filter having a pore diameter of 1.0 μm to make a coating solution.

A glass substrate on which an ITO film with a thickness of 150 nm was provided by sputtering was subjected to ozone-UV treatment for surface treatment. Next, the substrate was coated with the above coating solution by spin coating to obtain the activity layer (film thickness: about 100 nm) of an organic thin film solar cell. Then, the substrate was baked under conditions of 90° C. in a vacuum for 60 minutes. Then, lithium fluoride with a thickness of 4 nm was vapor-deposited by the vacuum deposition machine, and then, Al with a thickness of 100 nm was vapor-deposited. The degree of vacuum during vapor deposition was 1 to 9×10$^{-3}$ Pa for all. The shape of the obtained organic thin film solar cell was a 2 mm×2 mm square. The photoelectric conversion efficiency of the obtained organic thin film solar cell was obtained by emitting constant light using the solar simulator (manufactured by Bunkoukeiki Co., LTD., trade name: OTENTO-SUNII: AM1.5G filter, irradiance: 100 mW/cm$^2$), and measuring generated current and voltage. The results are shown in Table 3.

TABLE 3

| | Fullerene derivative | Photoelectric conversion efficiency (%) |
|---|---|---|
| Example 16 | I | 2.3 |
| Example 17 | J | 2.2 |
| Example 18 | K | 2.5 |
| Comparative Example 2 | [60] PCBM | 2.0 |

[60] PCBM (Phenyl C61-butyric acid methyl ester, manufactured by Frontier Carbon Corporation, trade name: E100)

—Evaluation—

As is seen from Table 1, the fullerene derivatives A to G had better solubility in xylene than [60]PCBM. Also, the organic thin film solar cells formed using the fullerene derivatives A, C, D, E, H, I, J, and K (Examples 8 to 12 and 16 to 18) exhibited high photoelectric conversion efficiency.

INDUSTRIAL APPLICABILITY

The organic photoelectric conversion device of the present invention has high conversion efficiency.

The invention claimed is:

1. A composition comprising a fullerene derivative represented by the following formula (1) and an electron-donating compound,

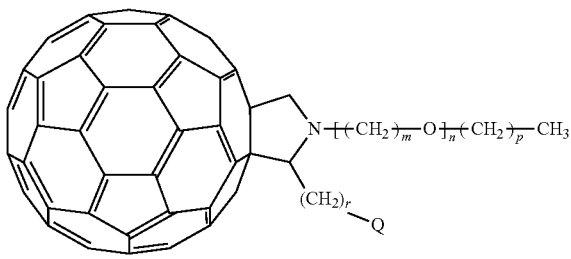

(1)

wherein m represents an integer of 1 to 6, n represents an integer of 2, p represents an integer of 0 to 5, and r represents an integer of 0 to 4; Q represents a group represented by the following formula (2) or (3); and when there is a plurality of m, the m may be the same or different,

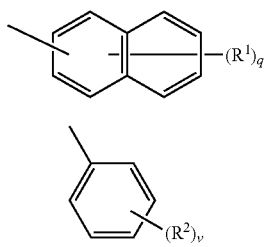

(2)

(3)

wherein $R^1$ and $R^2$ each independently represent a halogen atom, an alkyl group, an alkoxy group, or an aryl group; a hydrogen atom included in these groups may be replaced by a halogen atom; q represents an integer of 0 to 7, and v represents an integer of 0 to 5; when there is a plurality of $R^1$, the $R^1$ may be the same or different; and when there is a plurality of $R^2$, the $R^2$ may be the same or different.

2. The composition according to claim 1, wherein the electron-donating compound is a polymer compound.

3. An organic photoelectric conversion device comprising a layer comprising a composition according to claim 1.

4. A fullerene derivative represented by the following formula (4):

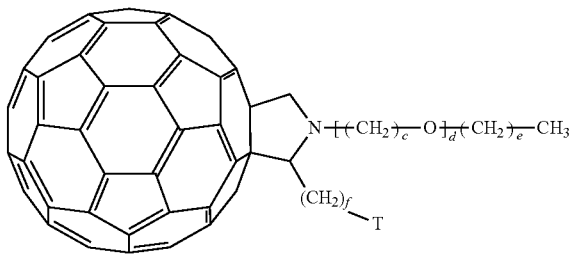

(4)

wherein c represents an integer of 1 to 6, d represents an integer of 2, e represents an integer of 0 to 5, and f represents an integer of 0 to 4; T represents a group represented by the following formula (5) or (6); and when there is a plurality of c, the c may be the same or different,

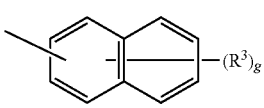

(5)

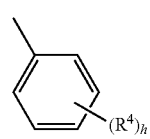

(6)

wherein $R^3$ and $R^4$ each independently represent a halogen atom, an alkyl group, an alkoxy group, or an aryl group; a hydrogen atom included in these groups may be replaced by a halogen atom; g represents an integer of 0 to 7, and h represents an integer of 0 to 5, provided that when h is 0, f is an integer of 1 to 4; when there is a plurality of $R^3$, the $R^3$ may be the same or different; and when there is a plurality of $R^4$, the $R^4$ may be the same or different.

5. An organic photoelectric conversion device comprising a layer comprising a composition according to claim 2.

* * * * *